US00PP29027P3

(12) United States Plant Patent
Palmer

(10) Patent No.: US PP29,027 P3
(45) Date of Patent: Feb. 27, 2018

(54) ***ARGYRANTHEMUM* PLANT NAMED 'G14420'**

(50) Latin Name: *Argyranthemum frutescens*
Varietal Denomination: G14420

(71) Applicant: Irene E. Palmer, Bellefonte, PA (US)

(72) Inventor: Irene E. Palmer, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 32 days.

(21) Appl. No.: 14/999,656

(22) Filed: Jun. 9, 2016

(65) Prior Publication Data

US 2017/0359939 P1 Dec. 14, 2017

(51) Int. Cl.
*A01H 5/02* (2006.01)

(52) U.S. Cl.
USPC ..... Plt./406

(58) Field of Classification Search
USPC ..... Plt./406
See application file for complete search history.

(56) References Cited

PUBLICATIONS

UPOV hit on *Argyranthemum* plant named 'G14420', CA PBR 16-8843, filed Mar. 30, 2016.*

* cited by examiner

*Primary Examiner* — Anne M Grunberg
(74) *Attorney, Agent, or Firm* — C. A. Whealy

(57) ABSTRACT

A new and distinct cultivar of *Argyranthemum* plant named 'G14420', characterized by its compact, upright and uniformly mounded plant habit; freely branching habit; dense and bushy appearance; freely flowering habit; large single-type inflorescences with white-colored ray florets; and good garden performance.

1 Drawing Sheet

Botanical designation: *Argyranthemum frutescens*.
Cultivar denomination: 'G14420'.

BACKGROUND OF THE INVENTION

The present invention relates to a new and distinct cultivar of *Argyranthemum* plant, botanically known as *Argyranthemum frutescens* and hereinafter referred to by the cultivar name 'G14420'.

The objective of the breeding program is to create new *Argyranthemum* plants with attractive ray and disc floret colors, sterility and good garden performance.

The new *Argyranthemum* plant is a naturally-occurring whole plant mutation of *Argyranthemum frutescens* 'Butterfly', not patented. The new *Argyranthemum* plant was discovered and selected by the Inventor as a single flowering plant from within a population of plants of 'Butterfly' in a controlled greenhouse environment in Bellefonte, Pa. in July, 2014.

Asexual reproduction of the new *Argyranthemum* plant by vegetative tip cuttings was first conducted in Bellefonte, Pa. on Nov. 17, 2014. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new *Argyranthemum* plant. These characteristics in combination distinguish 'G14420' as a new and distinct *Argyranthemum* plant:

1. Compact, upright and uniformly mounded plant habit.
2. Freely branching habit; dense and bushy appearance.
3. Freely flowering habit.
4. Large single-type inflorescences with white-colored ray florets.
5. Good garden performance.

Plants of the new *Argyranthemum* differ from plants of the mutation parent, 'Butterfly', in the following characteristics:

1. Plants of the new *Argyranthemum* have smaller and more dissected leaves than plants of 'Butterfly'.
2. Plants of the new *Argyranthemum* have larger inflorescences than plants of 'Butterfly'.
3. Ray florets of the new *Argyranthemum* are white in color whereas ray florets of plants of 'Butterfly' are yellow in color.

Plants of the new *Argyranthemum* can be compared to plants of *Argyranthemum frutescens* 'Vanilla', disclosed in U.S. Plant Pat. No. 14,642. In side-by-side comparisons, plants of the new *Argyranthemum* differ primarily from plants of 'Vanilla' in the following characteristics:

1. Plants of the new *Argyranthemum* have larger inflorescences than plants of 'Vanilla'.
2. Ray florets of the new *Argyranthemum* are white in color whereas ray florets of plants of 'Vanilla' are initially yellow in color and become creamy white in color with development.

Plants of the new *Argyranthemum* can also be compared to plants of *Argyranthemum frutescens* 'Bonmadwitim', disclosed in U.S. Plant Pat. No. 18,711. In side-by-side comparisons, plants of the new *Argyranthemum* differ primarily from plants of 'Bonmadwitim' in ratio of ray floret length to disc diameter as inflorescences of plants of 'Bonmadwitim' have ray florets that are approximately equal in length to the diameter of the disc whereas inflorescences of plants of the new *Argyranthemum* have ray florets that are approximately 1.5 times in length to the diameter of the disc.

BRIEF DESCRIPTION OF THE PHOTOGRAPHS

The accompanying photographs illustrate the overall appearance of the new *Argyranthemum* showing the colors as true as it is reasonably possible to obtain in colored reproductions of this type. Colors in the photographs may differ slightly from the color values cited in the detailed botanical description which accurately describe the colors of the new *Argyranthemum* plant.

The photograph at the bottom of the sheet comprises a side perspective view of a typical flowering plant of 'G14420' grown in a container.

The photograph at the top of sheet is a close-up view of a typical flowering plant of 'G14420'.

DETAILED BOTANICAL DESCRIPTION

The aforementioned photographs and following observations and measurements describe plants grown during the late summer 10-cm containers in an acrylic-covered greenhouse in Carleton, Mich. and under cultural practices typical of commercial potted *Argyranthemum* production. During the production of the plants, day and night temperatures ranged from 18° C. to 31° C. Plants were seven weeks old when the photographs and description were taken. In the following description, color references are made to The Royal Horticultural Society Colour Chart, 2007 Edition, except where general terms of ordinary dictionary significance are used.

Botanical classification: *Argyranthemum frutescens* 'G14420'.

Parentage: Naturally-occurring whole plant mutation of *Argyranthemum frutescens* 'Butterfly', not patented.

Propagation:

- *Type*.—Terminal vegetative cuttings.
- *Time to initiate roots, summer*.—About one to two weeks at soil temperatures about 22° C.
- *Time to initiate roots, winter*.—About two to three weeks at soil temperatures about 22° C.
- *Time to produce a rooted young plant, summer*.—About three to four weeks at ambient temperatures about 22° C. to 27° C.
- *Time to produce a rooted young plant, winter*.—About four to five weeks at ambient temperatures about 18° C. to 23° C.
- *Root description*.—Medium in thickness, fibrous; close to white in color, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Herbaceous perennial; compact, upright and uniformly mounding plant habit; moderately vigorous growth habit.
- *Branching habit*.—Freely branching growth habit with about four primary branches, each with about three to five secondary lateral branches developing per plant.
- *Plant height, soil level to top of foliar plane*.—About 15.8 cm.
- *Plant height, soil level to top of floral plane*.—About 21 cm.
- *Plant width*.—About 29.5 cm.
- *Lateral branches*.—Length: About 13.8 cm. Diameter: About 3 mm. Internode length: About 8 mm. Strength: Strong; young stems, flexible. Aspect: Highly variable, about 45° to about 70° from vertical. Texture: Smooth, glabrous. Luster: Semi-glossy. Color: Close to 145B; at the internodes, closer to 145A.

Leaf description:

- *Arrangement*.—Alternate, simple.
- *Length*.—About 5.5 cm.
- *Width*.—About 4.2 cm.
- *Shape*.—Pinnatisect; in outline, elliptical.
- *Apex*.—Acute.
- *Base*.—Attenuate.
- *Margin*.—Deeply dissected.
- *Sinuses*.—Parallel.
- *Texture, upper surface*.—Smooth, glabrous.
- *Texture, lower surface*.—Smooth, mostly glabrous with sparse pubescence along the veins.
- *Luster, upper and lower surfaces*.—Matte.
- *Venation*.—Pinnate.
- *Color*.—Developing leaves, upper and lower surfaces: Close to 146A to 146B. Fully expanded leaves, upper surface: Close to 137A; venation, close to 137B. Fully expanded leaves, lower surface: Close to 137B; venation, close to 137B.
- *Petioles*.—Length: About 2.8 cm. Diameter: About 4 mm. Strength: Moderately strong. Texture, upper and lower surfaces: Smooth, glabrous. Luster, upper and lower surfaces: Very slightly glossy. Color, upper surface: Close to 144A to 144B. Color, lower surface: Close to 144A.

Inflorescence description:

- *Inflorescence form and arrangement*.—Single-type terminal and axillary inflorescences held above and beyond the foliar plane on strong peduncles; ray and disc florets arranged acropetally on a receptacle; inflorescences face mostly upright to slightly outwardly.
- *Flowering habit*.—Freely flowering habit with about 22 inflorescence buds and open inflorescences per plant.
- *Flowering season*.—Plants flower from summer to late autumn in Pennsylvania; flowering continuous during this period.
- *Inflorescence longevity*.—Inflorescences last about five days on the plant; inflorescences persistent.
- *Fragrance*.—None detected.
- *Inflorescence buds*.—Height: About 1.6 cm. Diameter: About 1.1 cm. Shape: Ovoid. Texture: Smooth, glabrous. Luster: Matte. Color: Close to 145D.
- *Inflorescence size*.—Diameter: About 5.5 cm. Depth (height): About 1.7 cm. Diameter of disc: About 1.5 cm. Receptacle diameter: About 1.8 cm. Receptacle height: About 8 mm. Receptacle color: Close to 147B.

*Ray florets*.—Quantity per inflorescence and arrangement: About 20 arranged in about 1 to 1.5 whorls. Length: About 2.5 cm. Width: About 6 mm. Shape: Oblong. Apex: Minutely tri-dentate. Base: Attenuate. Margin: Entire. Aspect: Initially upright; arching slightly upward to nearly horizontal with development. Texture, upper and lower surfaces: Smooth, glabrous. Luster, upper and lower surfaces: Matte. Color: When opening, upper surface: Close to 157C. When opening, lower surface: Close to 157B. Fully opened, upper surface: Close to 155C; venation, close to 155C; color does not change with development. Fully opened, lower surface: Close to NN155B; venation, close to NN155B; color does not change with development.

*Disc florets*.—Quantity per inflorescence and arrangement: About 170 spirally arranged in about ten whorls at the center of the receptacle. Length: About 6 mm. Diameter: About 2 mm. Shape: Tubular with five free apical lobes. Apex: Acute. Texture, inner and outer surfaces: Smooth, glabrous. Luster, inner and outer surfaces: Slightly glossy. Color, immature and mature, inner and outer surfaces: Apex: Close to 17A. Mid-section and base: Close to 17B.

*Phyllaries*.—Quantity per inflorescence and arrangement: About 32 arranged in about three to four whorls. Length: About 4 mm. Width: About 2 mm. Shape: Elliptical. Apex: Acute. Base: Truncate. Margin: Entire. Texture, upper and lower surfaces: Smooth, glabrous; edges, membraneous. Luster, upper surface: Slightly glossy. Luster, lower surface: Matte. Color, upper and lower surfaces: Close to 144A.

*Peduncles*.—Length, terminal peduncle: About 6.7 cm. Diameter, terminal peduncle: About 2 mm. Length, third peduncle: About 7.8 cm. Diameter, third peduncle: About 2 mm. Angle: Terminal peduncle, erect; lateral peduncles, about 45° to 60° from primary lateral axis. Strength: Moderately strong. Texture: Smooth with shallow longitudinal ridges, glabrous. Luster: Matte. Color: Close to 146A.

*Reproductive organs*.—Androecium: Present on disc florets only; five per disc floret. Filament length: About 1.5 mm. Filament color: Close to 145C. Anther size: About 1.5 mm by less than 1 mm. Anther shape: Lanceolate. Anther color: Close to 15A. Pollen amount: Scarce. Pollen color: Close to 15A. Gynoecium: Present on both ray and disc florets; one per floret. Pistil length: About 5 mm. Stigma diameter: Less than 1 mm. Stigma shape: Bi-parted. Stigma color: Close to 13A. Style length: About 2 mm. Style color: Close to 151B. Ovary color: Close to 145A.

*Seeds and fruits*.—Seed and fruit production has not been observed on plants of the new *Argyranthemum*.

Disease & pest resistance: Plants of the new *Argyranthemum* have not been shown to be resistant to pathogens and pests common to *Argyranthemum* plants.

Garden performance: Plants of the new *Argyranthemum* have been observed to have good garden performance and to tolerate rain, wind and to tolerate low temperatures about 1.7° C.

It is claimed:

1. A new and distinct *Argyranthemum* plant named 'G14420' as illustrated and described.

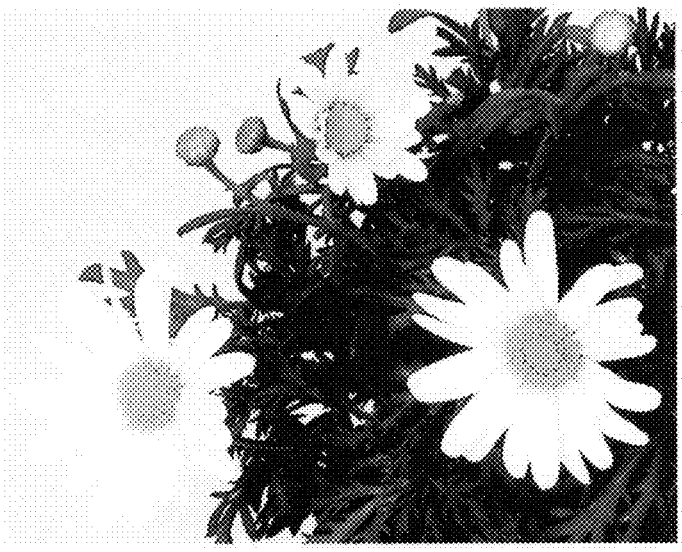
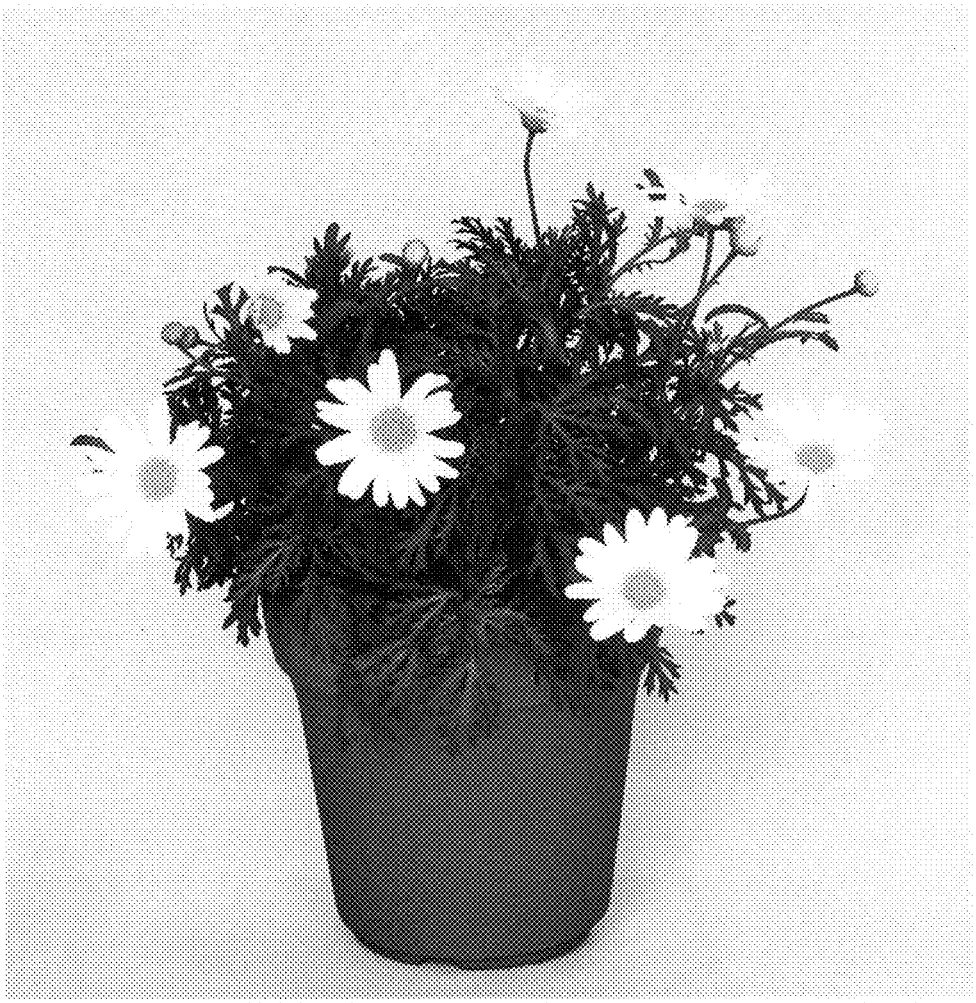

* * * * *